US007888305B2

(12) United States Patent
Lallier et al.

(10) Patent No.: US 7,888,305 B2
(45) Date of Patent: Feb. 15, 2011

(54) 1,1,1,3,3-PENTAFLUOROBUTANE COMPOSITION

(75) Inventors: Jean-Pierre Lallier, Saint Bonnet de Mure (FR); Christopher Bertelo, Doylestown, PA (US)

(73) Assignee: Arkema France, Colombes (FR)

( * ) Notice: Subject to any disclaimer, the term of this patent is extended or adjusted under 35 U.S.C. 154(b) by 644 days.

(21) Appl. No.: 11/658,423

(22) PCT Filed: Jul. 18, 2005

(86) PCT No.: PCT/FR2005/001828

§ 371 (c)(1),
(2), (4) Date: Jan. 26, 2007

(87) PCT Pub. No.: WO2006/024729

PCT Pub. Date: Mar. 9, 2006

(65) Prior Publication Data

US 2009/0005289 A1    Jan. 1, 2009

(30) Foreign Application Priority Data

Jul. 29, 2004    (FR) .................................. 04 08361

(51) Int. Cl.
*C11D 7/50* (2006.01)
(52) U.S. Cl. ................. 510/411; 510/365; 510/412
(58) Field of Classification Search ................. 510/365, 510/411, 412
See application file for complete search history.

(56) References Cited

U.S. PATENT DOCUMENTS

| 5,348,681 | A | | 9/1994 | Desbiendras et al. | |
|---|---|---|---|---|---|
| 5,350,534 | A | * | 9/1994 | Michaud | 510/177 |
| 5,445,757 | A | | 8/1995 | Pennetreau | |
| 5,478,492 | A | | 12/1995 | Barthelemy et al. | |
| 5,948,174 | A | * | 9/1999 | Barthelemy et al. | 134/42 |
| 6,174,850 | B1 | | 1/2001 | Michaud | |
| 6,489,277 | B1 | * | 12/2002 | Michaud | 510/175 |
| 6,660,709 | B1 | * | 12/2003 | Dournel et al. | 510/461 |
| 6,743,765 | B1 | * | 6/2004 | Dournel et al. | 510/461 |
| 7,022,253 | B2 | * | 4/2006 | Dournel et al. | 252/67 |
| 7,189,339 | B2 | * | 3/2007 | Dournel et al. | 252/67 |
| 7,517,845 | B2 | * | 4/2009 | Dournel et al. | 510/273 |
| 2004/0192573 | A1 | * | 9/2004 | Dournel et al. | 510/415 |
| 2004/0204330 | A1 | * | 10/2004 | Dournel et al. | 510/412 |
| 2004/0204512 | A1 | * | 10/2004 | Bogdan et al. | 521/99 |
| 2007/0135326 | A1 | * | 6/2007 | Dournel et al. | 510/407 |
| 2009/0005289 | A1 | * | 1/2009 | Lallier et al. | 510/412 |
| 2009/0048138 | A1 | * | 2/2009 | Lallier | 510/364 |
| 2009/0101177 | A1 | * | 4/2009 | Caron et al. | 134/22.14 |

* cited by examiner

*Primary Examiner*—Gregory E Webb
(74) *Attorney, Agent, or Firm*—Steven D. Boyd

(57) ABSTRACT

The invention relates to the field of solvents. The invention relates more particularly to a composition based on 1,1,1,3, 3-pentafluorobutane (HFC-365 mfc). The present invention also relates to a process for dissolving oil.

10 Claims, No Drawings

1,1,1,3,3-PENTAFLUOROBUTANE COMPOSITION

FIELD OF THE INVENTION

The invention relates to the field of solvents. The invention relates more particularly to a composition based on 1,1,1,3,3-pentafluorobutane (HFC-365 mfc). The present invention also relates to a process for dissolving oil.

BACKGROUND OF THE INVENTION

The power of a solvent is generally characterized by the kauri-butanol number, which is the volume in ml at 25° C. of a solvent required to produce a defined degree of turbidity when 20 g of a standard solution of kauri resin are added to n-butanol. This number is equal to 57 for 1,1-dichloro-1-fluoroethane (also known as HCFC-141b).

Besides its good solvent power, HCFC-141b is also characterized by a low surface tension (equal to 19.3 mN/m), which gives it a very good capacity for wetting surfaces. Since the boiling point of HCFC-141b is equal to 32° C., this allows it to evaporate quickly and thus to facilitate the deposition of dissolved products onto substrates. Finally, HCFC-141b has no closed-cup flash point and is therefore a non-flammable solvent.

HCFC-141b thus has properties that give it a good capacity for dissolving many organic compounds, especially silicone oils.

However, on account of its non-negligible action on the ozone layer (ozone degradation potential ODP=0.11), HCFC-141b is subject to major regulations that increasingly target its abolition. Thus, the European regulation on substances that are harmful to the ozone layer (No. 2037/2000) has banned the use of HCFCs (hydrochlorofluorocarbons) such as HCFC-141b in solvent applications since 1 Jan. 2002, except for the fields of aeronautics and aerospace, where the ban will take effect in Europe from 2009.

Document EP 974642 proposes an azeotropic composition of 1,1,1,3,3-pentafluorobutane (known under the name HFC-365 mfc) and of 1,1,1,2,3,4,4,5,5,5-decafluoropentane (known under the name HFC-4310 mee) as replacements for HCFC-141b on account of their absence of effect on the ozone layer. However, the kauri-butanol number of such a composition is much lower than that of HCFC-141b. The kauri-butanol number for HFC-365 mfc is 12, and is equal to 9 for HFC-4310 mee.

A composition comprising from 30% to 70% by weight of 1,1,1,3,3-pentafluorobutane and from 70% to 30% by weight of methylene chloride is moreover known (FR 2 694 942).

Moreover, in the context of environmental protection, the current tendency is towards reducing the emissions of solvent by evaporation. Thus, in many "emissive" applications, i.e. applications for which the solvent is liable to evaporate into the air, solvents that are effective at a temperature lower than room temperature are sought.

The present invention thus provides a composition comprising 1,1,1,3,3-pentafluorobutane, methylene chloride and at least one alcohol containing from 2 to 4 carbon atoms.

DETAILED DESCRIPTION OF THE INVENTION

Ethanol, propanol, isopropanol, butanol, secondary butanol (sec-butanol) or tert-butanol may be suitable. Isopropanol or secondary butanol is preferably used.

The total amount of alcohol present in the composition according to the invention is preferably between 1% and 10% by weight.

The present invention most particularly provides:

1) a composition comprising from 27% to 69% by weight of HFC-365 mfc, from 69% to 27% by weight of methylene chloride and from 1% to 10% by weight of alcohol, preferably from 1% to 5% by weight of alcohol;

2) a composition comprising from 47.5% to 60% by weight of HFC-365 mfc, from 35% to 47.5% by weight of methylene chloride and from 1% to 5% by weight of alcohol.

The compositions according to the present invention may be prepared by mixing together the various constituents. They are advantageously prepared by adding at least one alcohol containing from 2 to 4 carbon atoms to an azeotropic or virtually azeotropic composition of HFC-365 mfc and of methylene chloride.

The compositions according to the present invention have good solvent power and good surface wettability and, furthermore, are non-flammable.

The compositions according to the present invention may be used in industry for cleaning, degreasing and drying a wide variety of solid surfaces (metal components, glasses, plastics and composites). They may also be used in the manufacture of printed circuits to remove the residues of the substances used to improve the quality of the welds. This removal operation is referred to in the art as "defluxing".

The compositions according to the present invention may advantageously be used to deposit medical-grade silicone oils onto instruments, for example onto syringe needles or catheter needles. In addition, they may be used to deposit silicone oils onto kitchen utensils.

These compositions may also be used as agents for depositing silicone-based greases or polymers or in formulations for cleaning components coated with silicone oils or greases.

The compositions according to the present invention may also be used for dissolving silicone oils included in the formulation of antiadhesive agents (which are often in the form of aerosols) for moulds in processes for manufacturing plastic components (extrusion).

The compositions may also be used as polyurethane foam expanders, as aerosols propellants, as heat-exchange fluids, as textile dry-cleaning agents or as agents for cleaning refrigeration plants.

A subject of the present invention is also a process for dissolving oil. This process is characterized in that a composition comprising 1,1,1,3,3-pentafluorobutane, methylene chloride and at least one alcohol containing from 2 to 4 carbon atoms is used.

The process according to the present invention is preferably performed at a temperature below 10° C. A temperature of between 0 and 8° C. is also preferred. A temperature of between 3 and 6° C. is advantageously chosen.

This process is most particularly suitable for dissolving silicone oil.

The composition according to point 1) is most particularly suitable for performing the process. The composition according to point 2) is preferred.

This process is of major interest, especially in the medical field, when isopropanol or sec-butanol is present in the composition used.

EXPERIMENTAL SECTION

The following compositions were prepared:

Composition A: Azeotropic of 57% by weight of HFC 365 mfc and 43% by weight of methylene chloride Composition B: 95% by weight of Composition A and 5% by weight of sec-butanol Composition C: 95% by weight of Composition A and 5% by weight of isopropanol.

EXAMPLE 1

Description of the Silicone Oil Dissolution Tests

A silicone oil Crompton L9000-1000 from the company Crompton Corporation (Greenwich, USA) is used. This is a transparent liquid hydroxypolydimethylsiloxane with a density of 0.97 at room temperature (22° C.), a boiling point of greater than 200° C. and a flash point of 132° C. (Pensky-Martens method, in a closed cup).

Mixtures are prepared at room temperature, i.e. at 22° C.

Thus, 18 ml of the test composition and 1.94 g of silicone oil are introduced into a 50 ml flask, i.e. a 10 vol % solution is prepared. The mixture is then stirred manually for five minutes.

A portion of the mixture thus prepared is kept at rest at room temperature (22° C.) for 24 hours. Another portion is kept at rest at low temperature (6° C.) for seven days.

After the period of storage at different temperatures, the appearance of the mixture is observed precisely. It is considered that there is solubility at room temperature or at 6° C. when the mixture is transparent, clear, homogeneous, monophasic and stable.

Results

| Composition | Solubility at 22° C. | Solubility at 6° C. |
| --- | --- | --- |
| HCFC-141b | YES | YES |
| Composition A | YES | NO |
| Composition B | YES | YES |
| Composition C | YES | YES |

EXAMPLE 2

Description of the Flammability Test

To evaluate the flammability of the compositions, we determined their flash point according to the standardized method ASTM D 3828, Setaflash closed cup. The flash point is the minimum temperature at which a liquid releases vapours in an amount sufficient to form at the surface a mixture that is flammable in air under the action of a source of ignition, but without persistence of flames when the activation energy is withdrawn.

For each of the compositions, the measurement was repeated five times.

Results

| Composition | FLASH POINT |
| --- | --- |
| HCFC 141b | NO |
| Composition A | NO |
| Composition B | NO |
| Composition C | NO |

The invention claimed is:

1. Composition comprising 1,1,1,3,3-pentafluorobutane, methylene chloride and at least one alcohol chosen from isopropanol or sec-butanol.

2. Composition according to claim 1, characterized in that the total amount of alcohol is between 1% and 10% by weight.

3. Composition according to claim 1, characterized in that it comprises from 27% to 69% by weight of HFC-365 mfc, from 69% to 27% by weight of methylene chloride and from 1% to 10% by weight of alcohol.

4. Composition according to claim 1, characterized in that it comprises from 47.5% to 60% by weight of HFC-365 mfc, from 35% to 47.5% by weight of methylene chloride and from 1% to 5% by weight of alcohol.

5. Process for dissolving oil, comprising contacting oil with a composition comprising 1,1,1,3,3-pentafluorobutane, methylene chloride and at least one alcohol chosen from isopropanol or sec-butanol at a temperature below 10° C.

6. Process according to claim 5, characterized in that the temperature is between 3 and 6° C.

7. Composition according to claim 1, characterized in that the total amount of alcohol is between 1% and 5% by weight.

8. Composition according to claim 1, characterized in that it comprises from 27% to 69% by weight of HFC-365 mfc, from 69% to 27% by weight of methylene chloride and from 1% to 5% by weight of alcohol.

9. Process according to claim 5, characterized in that it is performed at a temperature between 0 and 8° C.

10. Process according to claim 5 wherein said oil is silicone oil.

* * * * *